(12) United States Patent
Nakatomi et al.

(10) Patent No.: US 6,881,721 B2
(45) Date of Patent: Apr. 19, 2005

(54) MEDICINAL COMPOSITIONS FOR TREATING AND PREVENTING DISEASES BASED ON ABNORMAL BLOOD COAGULATION

(75) Inventors: Yasushi Nakatomi, Kumamoto (JP); Kazuhiko Tomokiyo, Kumamoto (JP); Tatsuya Araki, Kumamoto (JP); Kaori Teshima, Kikuchi-gun (JP); Tomoko Watanabe, Kikuchi-gun (JP); Tomohiro Nakagaki, Kikuchi-gun (JP)

(73) Assignee: Juridical Foundation the Chemo-Sero-Therapeutic Research Institute, Kumamoto-ken (JP)

( * ) Notice: Subject to any disclaimer, the term of this patent is extended or adjusted under 35 U.S.C. 154(b) by 0 days.

(21) Appl. No.: 10/168,371

(22) PCT Filed: Dec. 21, 2000

(86) PCT No.: PCT/JP00/09102

§ 371 (c)(1),
(2), (4) Date: Aug. 20, 2002

(87) PCT Pub. No.: WO01/47548

PCT Pub. Date: Jul. 5, 2001

(65) Prior Publication Data

US 2003/0060411 A1 Mar. 27, 2003

(30) Foreign Application Priority Data

Dec. 24, 1999 (JP) .......................................... 11-368122

(51) Int. Cl.$^7$ ............................................. A61K 38/00
(52) U.S. Cl. ..................................................... 514/12
(58) Field of Search ........................................... 514/12

(56) References Cited

U.S. PATENT DOCUMENTS

| | | | |
|---|---|---|---|
| 4,286,056 A | | 8/1981 | Andary et al. |
| 4,287,180 A | | 9/1981 | Thomas |
| 4,357,321 A | * | 11/1982 | Thomas .................... 424/94.64 |
| 4,459,288 A | * | 7/1984 | Thomas .................... 424/94.64 |
| 4,663,164 A | | 5/1987 | Thomas |
| 5,891,843 A | * | 4/1999 | Turecek et al. ................. 514/2 |
| 6,083,905 A | * | 7/2000 | Voorberg et al. .............. 514/2 |

FOREIGN PATENT DOCUMENTS

| | | |
|---|---|---|
| EP | 651054 A1 | 5/1995 |
| EP | 765669 A1 | 2/1997 |
| JP | 3-155797 A | 7/1991 |
| JP | 7-145072 A | 6/1995 |
| JP | 7-145073 A | 6/1995 |
| JP | 7-145074 A | 6/1995 |
| JP | 7-145075 A | 6/1995 |
| JP | 10-59866 A | 3/1998 |
| JP | 10-59867 A | 3/1998 |

OTHER PUBLICATIONS

Y. Sultan et al.; Thrombosis and Haemostasis; vol. 67(6), pp. 600–602; 1992.
S. Ehrenforth et al.; The Lancet; vol. 339, pp. 594–598, 1992.
G. L. Bray et al.; Blood, vol. 83, No. 9, May 1, 1994, pp. 2428–2435.
David Green et al.; Thrombos. Haemostas.; vol. 45(3), pp. 200–203, 1981.
Stephen Chavin et al.; The American Journal of Medicine; vol. 85, pp. 245–249, 1988.
Thromb. Haemost.; vol. 48(3), pp. 339–340, 1982.
Ulla Hedner et al.; Transfusion Medicine Reviews, vol. VII, No. 2, Apr. 1993, pp. 78–83.
Hidehiko Saito et al.; Jpn. J. Thromb. Hemost., vol. 5(3), pp. 158–172, 1994.
D.S.C Telgt et al.; Thrombosis Research, vol. 56, pp. 603–609, 1989.
Haemostasis; vol. 26, (Supp. 1); pp. 143–149, 1996.
Kamiya T. et al., International Journal of Hematology, 1995, vol. 62, No. 3, pp. 175–181.
D.M. Monroe et al.; Blood Coagulation & Fibrinolysis, vol. 9, No. SUPPL 1, 1998, pp. S15–S–20.
G.A. Allen et al.; Blood Coagulation and Fibrinolysis, vol. 11, No. Supplement 1, Apr. 2000, pp. S3–S7. (After Priority Date).
K. Tomokiyo et al.; Vox Sanguinis, vol. 85, No. 4, Nov. 2003, pp. 290–299. (After Priority Date).

* cited by examiner

Primary Examiner—Christopher R. Tate
Assistant Examiner—Maury Audet
(74) Attorney, Agent, or Firm—Birch, Stewart, Kolasch & Birch, LLP

(57) ABSTRACT

The present invention provides a pharmaceutical composition for treatment and prevention of hemorrhage associated with blood coagulation disorders, comprising activated Factor VII (FVIIa) and Factor X (FX) as an active ingredient. The pharmaceutical composition of the present invention contains no components causative side effects, is safe, highly efficacious, and easy to manage hemostasis. The pharmaceutical composition can be used for hemostatic management of patients suffering from hemorrhage associated with blood coagulation disorders, for example, disorders (including deficiency) of blood coagulation factors, especially caused by inhibitors (antibodies) against blood coagulation factors.

5 Claims, 12 Drawing Sheets

Fig. 1 Blood Coagulation Cascade: Roman numerals indicate blood coagulation factors wherein suffix "a" represents activated form. PL: Phospholipid

MEDICINAL COMPOSITIONS FOR TREATING AND PREVENTING DISEASES BASED ON ABNORMAL BLOOD COAGULATION

This application is the national phase under 35 U.S.C. § 371 of PCT International Application No. PCT/JP00/09102 which has an International filing date of Dec. 21, 2000, which designated the United States of America.

TECHNICAL FIELD OF THE INVENTION

The present invention relates to a medicament for use in hemostatic management of patients suffering from blood coagulation disorders such as disorders (including deficiency) of blood coagulation factors, especially by possessing inhibitors to blood coagulation factors. More particularly, the present invention relates to a pharmaceutical composition for treatment and prevention of hemorrhage associated with blood coagulation disorders, said composition comprising as active ingredients activated Factor VII (hereinafter also referred to as "FVIIa") and Factor X (hereinafter also referred to as "FX").

BACKGROUND OF THE INVENTION

Hemostatic reaction is one of the most important protection mechanisms in the living body. It generally consists of primary hemostasis wherein platelets adhere and agglutinate to impaired portions of the blood vessel and secondary hemostasis wherein soluble fibrinogens are transformed into insoluble fibrins to plug the impaired portions. The process of secondary hemostasis is accomplished by successive reactions known as a blood coagulation cascade by a variety of blood coagulation factors and cofactors and has two courses, the intrinsic and extrinsic coagulation pathways (FIG. 1). Thus, if any factor or cofactor in the blood coagulation cascade is deficient or does not work properly, blood coagulation is hindered to lead hemorrhage. In most of these diseases, genetic disposition is traced and typical diseases caused by congenital disorder in blood coagulation factors are hemophilia A and B, deficient in Factor VIII and Factor IX, respectively.

For treating patients suffering from hemophilia, there have been developed concentrated preparations that comprise Factor VIII or Factor IX for supplement of the deficient factors and are used for hemostatic management, known as supplemental therapy. However, it is known that antibodies against Factor VIII or Factor IX, usually referred to as "inhibitors", are produced in about 2 to 24% of the patients subject to supplemental therapy (Thromb. Haemost. 67: 600–602 (1992); Int. J. Hematol. 62: 175–181 (1995); Lancet 339 (8793): 594–598 (1992); and Blood 83: 2428–2435 (1994)), which is one of the most serious side effects of supplemental therapy. Once inhibitors are produced in patients, supplemental therapy becomes ineffective to lead to extreme difficulty in hemostatic management. There are also many reports as to inhibitors that are induced spontaneously or in a way of autoimmune disease even in the absence of genetic disposition such as hemophilia (Thromb. Haemost. 45: 200–203 (1981)).

Principal therapies currently used for treating patients who possess inhibitors are as follows:

(a) Neutralizing Therapy:

An overdose of concentrated preparations that surpasses inhibitors is administered to neutralize inhibitors and factors necessary for hemostasis are supplemented.

(b) By-pass Therapy

As Factor VIII and Factor IX are both involved in the intrinsic coagulation pathway, hemostasis is effected not through (i.e. "bypassing") the intrinsic coagulation pathway but by the extrinsic coagulation pathway. For enhancement of capacity of the extrinsic coagulation pathway, activated prothrombin complex concentrate, called "APCC", or FVIIa preparations are administered.

(c) Immune Tolerance Therapy

Concentrated preparations are administered at high dose in a long spell so that ability of patients to produce inhibitors becomes immunologically impoverished, leading to disappearance of the antibodies.

However, the conventional therapies as mentioned above hold disadvantages in several points. Neutralizing therapy (a) is only efficacious to patients with a lower titer of inhibitors but ineffective to patients with a higher titer of inhibitors.

In by-pass therapy (b), APCC has been reported to cause side effects such as myocardial infarction (Am. J. Med. 85: 245–249 (1988)) or DIC (Thromb. Haemost. 48: 339–340 (1982)) to raise safety problem. On the other hand, FVIIa preparations are disadvantageous in that it must be administered frequently due to short half-life of FVIIa (Transfus. Med. Rev. 7: 78–83 (1993)), charging patients with much burden physically as well as economically for high cost of the drug. Moreover, FVIIa preparations are not sufficiently efficacious. Immune tolerance therapy (c) can only be efficacious to a limited number of patients and also charges economical burden to patients.

As such, the conventional methods for hemostatic management of patients who possess inhibitors are not sufficiently efficacious and hence there exist needs for preparations that are safer, more efficacious, and easy for hemostatic management.

Prior art includes Japanese patent publication Nos. 145072/1995 to 145075/1995 entitled "Aqueous Composition for Treatment of Blood Coagulation Factor Inhibitor" wherein an activation level in the conventional APCC is explored but active substances responsible for bypassing activity is not clarified. Another prior art is Japanese patent publication No. 110715/1997 entitled "Pharmaceutical Composition for Treatment of Blood Coagulation Disorders and Process for Preparation thereof" wherein a content of FVIIa in the APCC is increased so that a treatment efficacy is enhanced. This composition, however, is merely addition of FVIIa that is confirmed to be efficacious when used alone to the APCC and hence still holds drawbacks as mentioned above.

DISCLOSURE OF THE INVENTION

In light of the problems as mentioned above, the present inventors have investigated in order to develop a medicament for treatment and prevention of hemorrhage accompanied with blood coagulation disorders. As a result, the present inventors have unexpectedly found for the first time that a pharmaceutical composition comprising a combination of FVIIa and FX is remarkably efficacious for treatment and prevention of hemostatic disorders caused by blood coagulation disorders to complete the present invention.

Advantages of the pharmaceutical composition according to the present invention are: (1) it is entirely safe since it contains substantially no prothrombin, thrombin, Factor IX, activated Factor IX, phospholipids and the like, which were contained in the conventional APCC and considered to be causative agents of side effects; and (2) it does not need frequent administration, the drawback of the FVIIa preparations, and besides shows higher hemostatic effects than the FVIIa preparations. As a whole, the pharmaceutical composition of the present invention is a long-awaited medicament that is safe, highly efficacious, and easy to manage hemostasis. It is quite distinct from the conventional APCC in that it contains substantially no FII and FIX, and from the FVIIa preparations in that it contains FX.

BEST MODE FOR CARRYING OUT THE INVENTION

Figure 1:
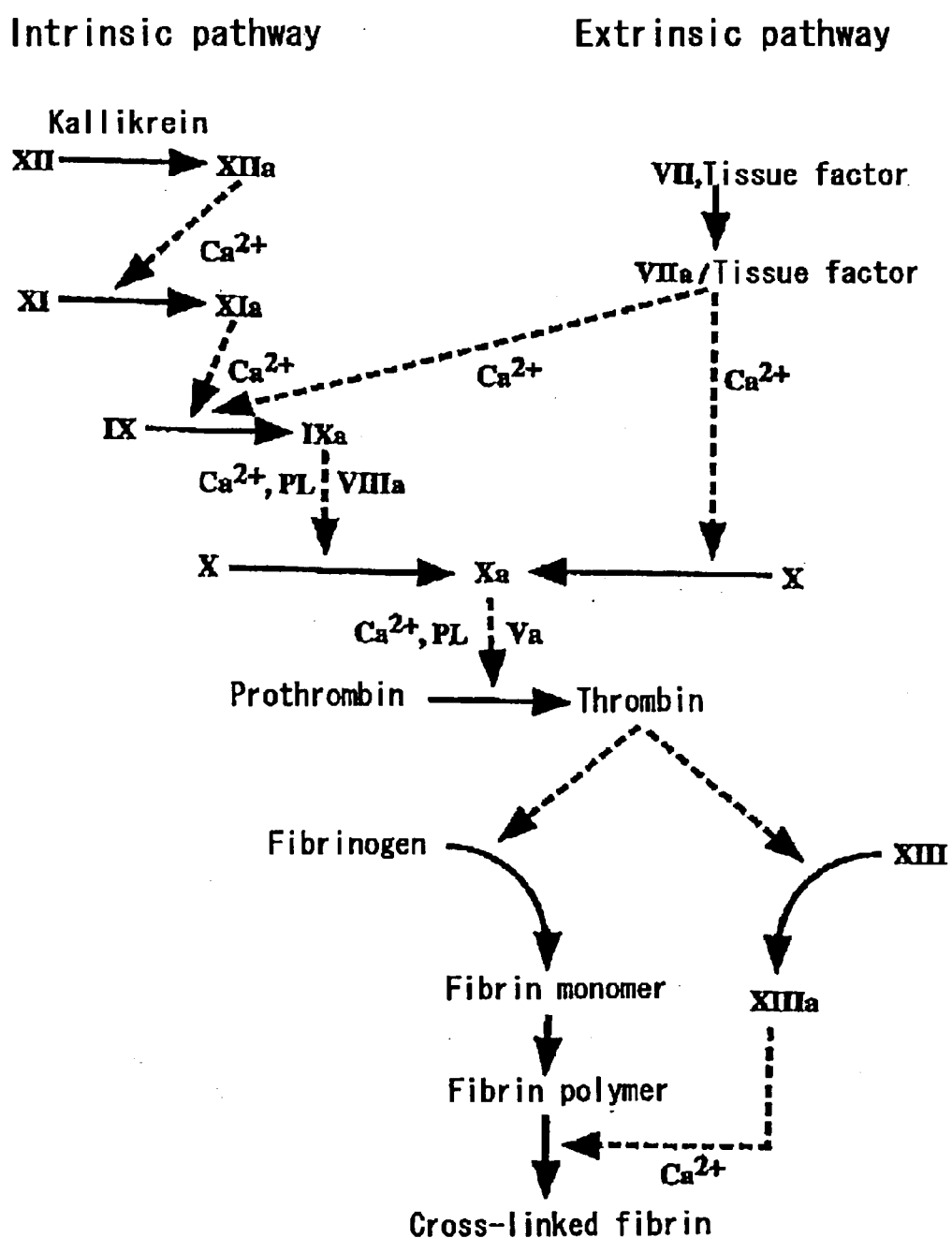
FIG. 1 is a schematic illustration of blood coagulation cascade wherein two pathways, the intrinsic and extrinsic coagulation pathways, are indicated.
Figure 2:
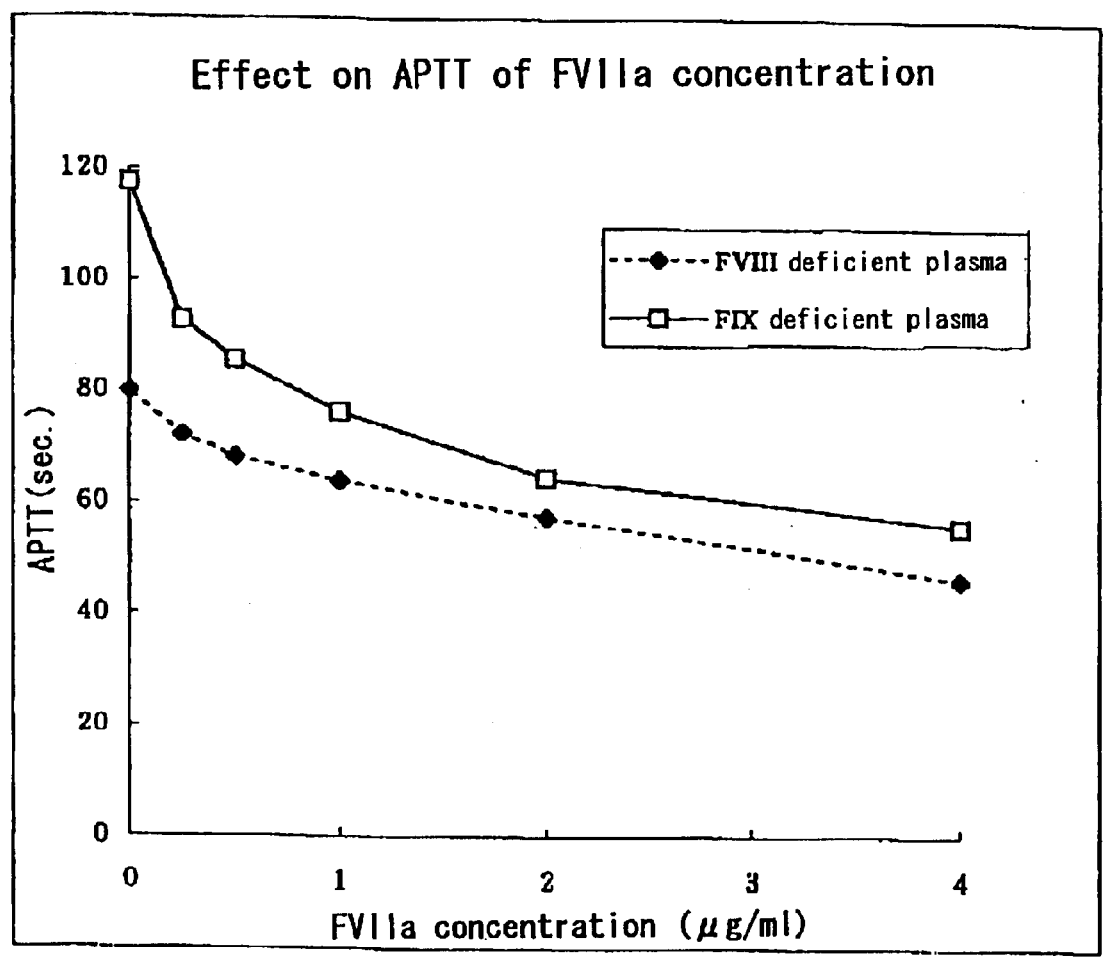
FIG. 2 is a graph showing effects of FVIIa on APTT in FVIII or FIX deficient plasma.
Figure 3:
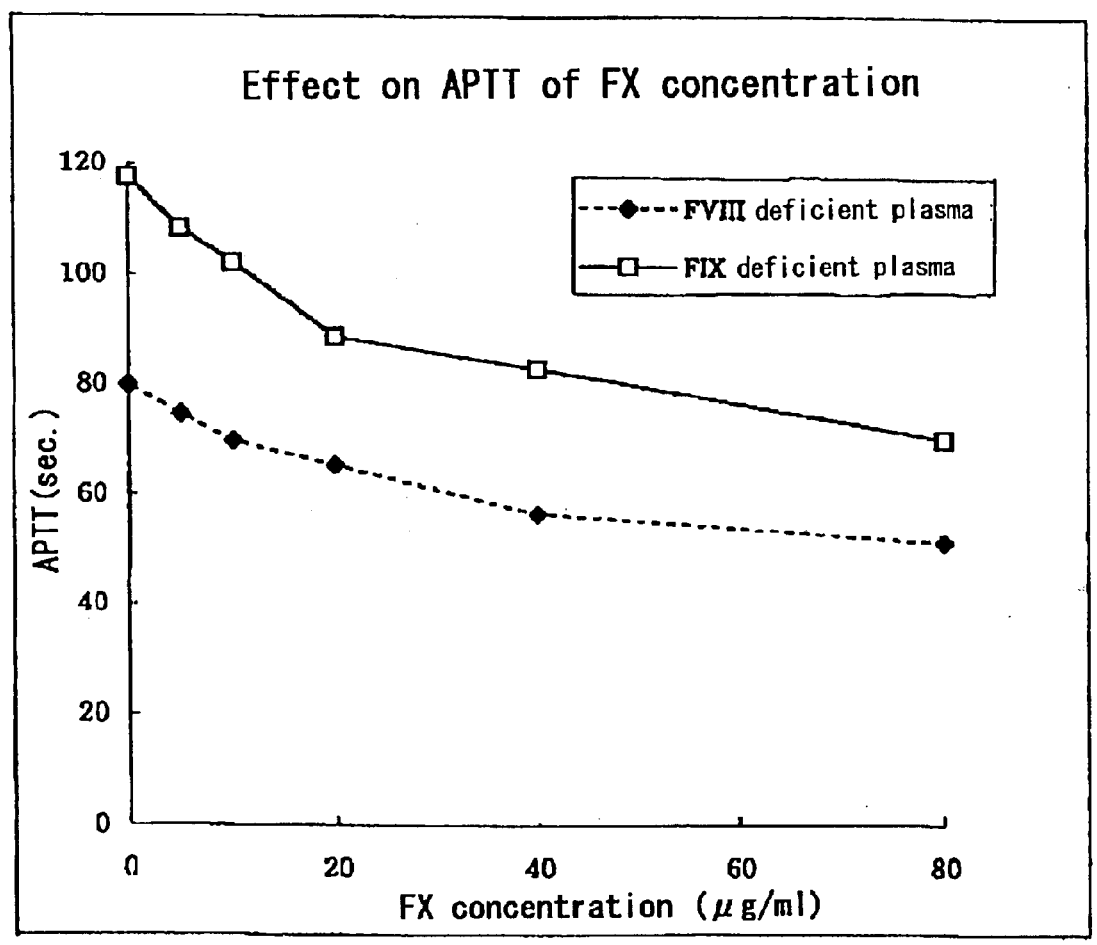
FIG. 3 is a graph showing effects of FX on APTT in FVIII or FIX deficient plasma.
Figure 4:
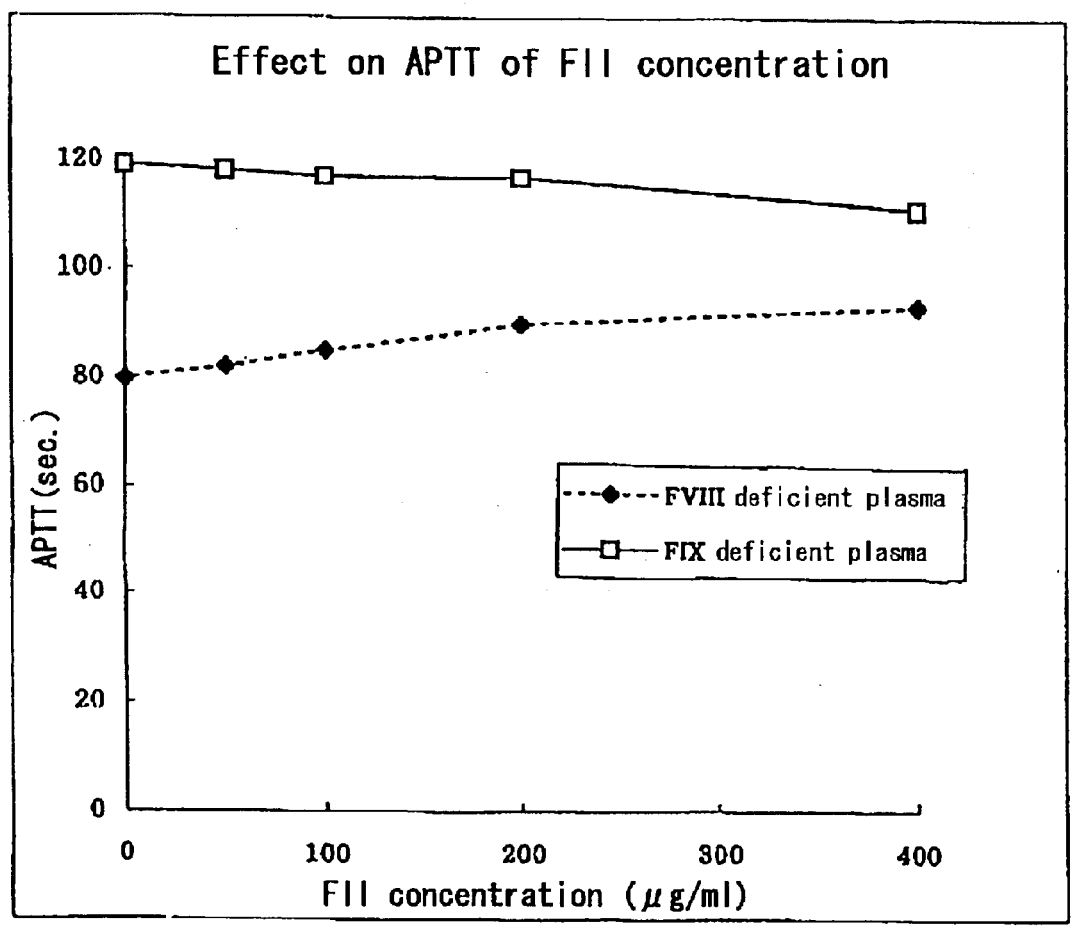
FIG. 4 is a graph showing effects of FII on APTT in FVIII or FIX deficient plasma.
Figure 5:
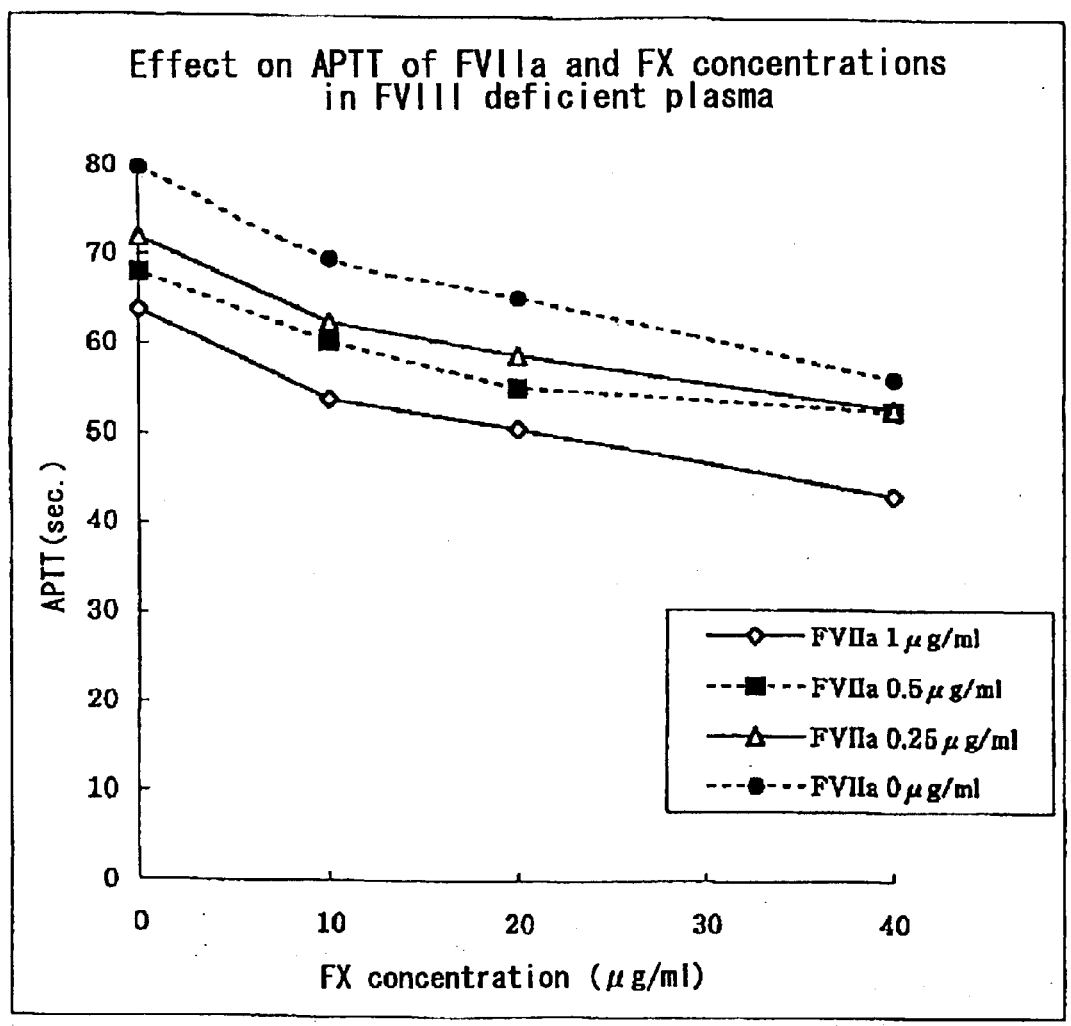
FIG. 5 is a graph showing synergic effects of FVIIa and FX on APTT in FVIII deficient plasma.
Figure 6:
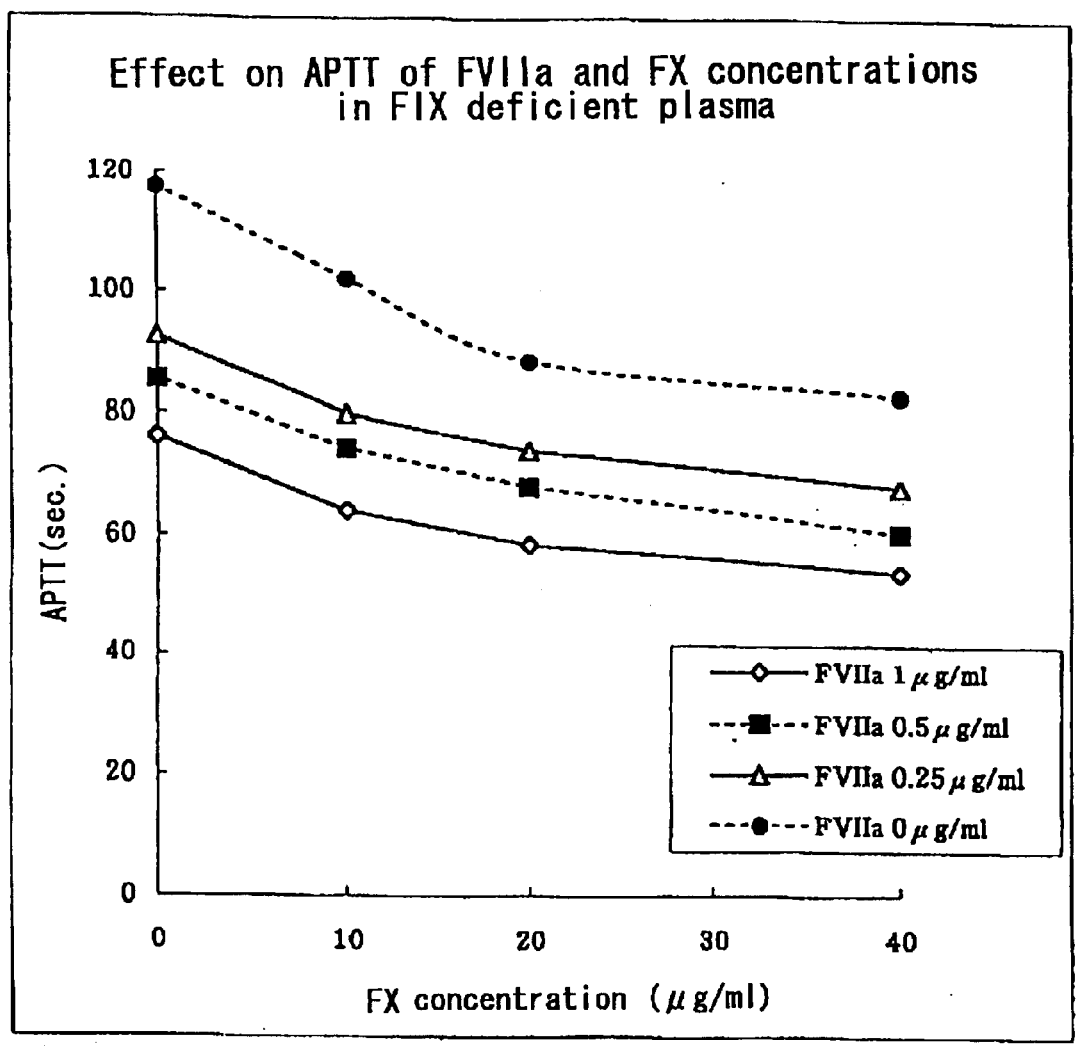
FIG. 6 is a graph showing synergic effects of FVIIa and FX on APTT in FIX deficient plasma.

FVII, a precursor of one of active ingredients of the pharmaceutical composition of the present invention, is a vitamin K dependent coagulation factor consisted of 406 amino acid residues with a molecular weight of about 50,000. In plasma, FVII is present at about 0.5 $\mu$g/ml. FVII, when hydrolyzed at Arg152-Ile153 bondage in the molecule, is converted into two-chain FVIIa with enzymatic activity. FVIIa in combination with a tissue factor activates FIX and FX in the presence of calcium ions. Thus, FVIIa plays a most important role in the extrinsic coagulation pathway.

On the other hand, FX is also a vitamin K dependent blood coagulation factor consisted of 448 amino acid residues with a molecular weight of about 59,000 and present at 5 to 10 $\mu$g/ml in plasma. FX is converted into activated FX (hereinafter also referred to as "FXa") with enzymatic activity through activation either by FVIIa/tissue factor complex in the presence of calcium ions (extrinsic coagulation pathway) or by activated Factor IX in the presence of activated Factor VIII, calcium ions and phospholipids (intrinsic coagulation pathway). FXa then activates prothrombin into thrombin in the presence of activated Factor V, calcium ions and phospholipids to thereby induce fibrin formation.

FVIIa and FX as used in the present invention may be prepared by any method known in the art including isolation from human blood or with the use of the genetic recombination technique.

FVIIa may be prepared from blood by the methods, for example, as disclosed in Japanese Patent Publications No. 155797/1991, No. 059866/1998 and No. 059867/1998. Alternatively, cryoprecipitate poor plasma, prepared by thawing at low temperature and centrifugation of fresh frozen human plasma to remove cryoprecipitate, is subject to anion exchange chromatography to produce crudely purified FVII, which is then further purified by affinity chromatography using a column with immobilized anti-FVII monoclonal antibody. The resulting purified FVII is then activated by other plasma proteins, e.g. activated Factor XII or FXa, into FVIIa. For safety purpose, preferably the resulting FVIIa is contaminated with as little FII, FIIa, FIX and FIXa as possible.

For preparation of FX from blood, for example, cryoprecipitate poor plasma, prepared by thawing at low temperature and centrifugation of fresh frozen human plasma to remove cryoprecipitate, is subject to anion exchange chromatography to produce crudely purified FX, which is then further purified by affinity chromatography using a column with immobilized anti-FX monoclonal antibody. As described above for FVIIa, preferably the resulting FX is contaminated with as little FII, FIIa, FIX and FIXa as possible to ensure safety.

Each of the thus prepared FVIIa and FX may be stored by freeze-drying with appropriate stabilizing agents to ensure maintenance of the activity of FVIIa and FX at maximum level. Alternatively, a solution of FVIIa or FX may be freeze-dried for storage. It is also possible to freeze-dry FVIIa and FX in admixture with appropriate stabilizing agents at a suitable concentration for storage or to freeze-dry a mixture of FVIIa and FX solutions.

In accordance with the present invention, a composition comprising FVIIa or FX as an active ingredient is combined with a suitable excipient known in the art to formulate a medicament for treatment and prevention of hemostatic disorders caused by blood coagulation disorders by using the art-known processes. The medicament of the present invention may be administered to any patients as far as they suffer from hemostatic disorders caused by blood coagulation disorders.

Although an effective dose of FVIIa and FX may vary depending on, for example, age of patient, symptoms and severity of diseases, hemostatic effect is anticipated with FVIIa at 5 $\mu$g/body weight (kg) to 160 $\mu$g/body weight (kg) and FX at 50 $\mu$g/body weight (kg) to 16,000 $\mu$g/body weight (kg). FVIIa and FX may most suitably be administered with single administration (Bolus) or by intravenous drip injection.

In a preferable embodiment, the medicament for treatment and prevention of hemostatic disorders according to the present invention comprises both FVIIa and FX as active ingredients. In another embodiment, however, FVIIa and FX may separately be administered if an interval between the two administrations is short enough to thereby exert the effects of the present invention.

The present invention is explained in more detail by means of the examples mentioned below.

EXAMPLE 1
Estimate for Hemostatic Potency of the Composition of the Present Invention by APTT Assay:

"Activated Partial Thromboplastin Time" (hereinafter also referred to as "APTT") is a test method for screening the intrinsic pathway using an APTT reagent. Specifically, an APTT reagent and calcium ions are added to test plasma and fibrin formation time is measured to estimate enzymatic potency in the intrinsic coagulation pathway. APTT is prolonged when intrinsic blood coagulation factors have quantitative or qualitative abnormalities as in typically hemophilia A and B or inhibitors to intrinsic blood coagulation factors are present.

Normal time of APTT is 30 to 40 seconds and a rate of prolonged APTT is dependent on the clotting activities of intrinsic coagulation factors with quantitative or qualitative abnormalities. In case of hemophilia with clinically severe symptoms, including inhibitors, APTT is extraordinarily prolonged. According to clinical estimate of FVIIa preparations reported by Saito et al. (Jpn. J. Thromb. Hemost. 5(3): 158–172 (1994)), APTT was prolonged to 122.0±18.7 seconds (mean±SD) in twelve hemophilia patients with inhibitors. However, twenty minutes after administration of genetically engineered FVIIa, it was shortened to 82.9±21.6 seconds. It was also reported that APTT was significantly lowered in vitro when FVIIa was added to plasma that was deficient in FVIII or FIX (Thromb. Res. 56: 603–609 (1989)).

In this example, using Factor VIII or Factor IX deficient plasma (manufactured by Dade Behring Marburg GmbH) as hemophilia-like plasma, effects of FVIIa, FX and FII to shorten APTT were estimated. For an APTT reagent, Actin (trade name) (manufactured by Dade Behring Marburg GmbH) was used. The coagulation factors were estimated at a final concentration of 0 to 4 µg/ml plasma for FVIIa; 0 to 80 µg/ml plasma for FX (normal level in human plasma: about 10 µg/ml plasma); and 0 to 400 µg/ml plasma for FII (normal level in human plasma: about 100 µg/ml plasma). The results are shown in FIGS. 2 to 6 in which FIGS. 2 to 4 indicate effects on APTT of each of FVIIa, FX and FII in the deficient plasma in a concentration dependent manner whereas FIGS. 5 and 6 indicate synergic effects of a combination of FVIIa and FX on APTT in the deficient plasma.

It was found that FVIIa and FX both shortened APTT in the deficient plasma in a concentration dependent manner while FII could scarcely shorten APTT. A combination of FVIIa and FX was also tested using a final concentration of 0 to 1 µg/ml in plasma and 0 to 40 µg/ml in plasma, respectively, which were added simultaneously to the deficient plasma to estimate APTT correction. It was revealed that FVIIa and FX at a higher concentration were likely to shorten APTT to a higher extent. Moreover, as compared to effects observed when either FVIIa or FX was used alone, much higher effects were observed when these blood coagulation factors were combined, proving remarkable synergic effects.

EXAMPLE 2
Estimate for Hemostatic Potency of the Composition of the Present Invention by Thromboelastgram:

"Thromboelastgram" (hereinafter also referred to as "TEG"), which measures viscoelastic change in blood coagulation process, provides patterns specific to various blood coagulation disorders and is used to determine clotting capacity of blood. In case of hemophilia or in the presence of inhibitors to intrinsic blood coagulation factors, abnormal TEG patterns are exhibited due to inhibition of blood coagulation. Numerically, TEG parameters, "r" (reaction time), and "r+k" (k: coagulation time), are varied with "r" in normal human plasma being 10 to 15 minutes, "k" 6 to 8 minutes and "r+k" 16 to 23 minutes. In case of hemophilia or in the presence of inhibitors to intrinsic blood coagulation factors, these parameters fall without the indicated normal range and are markedly prolonged. According to report by Yoshioka et al. (Haemostasis 26 (suppl 1): 143–149 (1996)), administration of FVIIa preparations to patients suffering from hemophilia A inhibitor almost restored normal level from the so far prolonged parameters, "r" (more than 60 minutes) and "r+k" (more than 80 minutes), while "r" and "r+k" were again prolonged with decrease of FVIIa level in the living body. This demonstrates that measurement of TEG may advantageously used for estimating capacity of blood.

Figure 7:
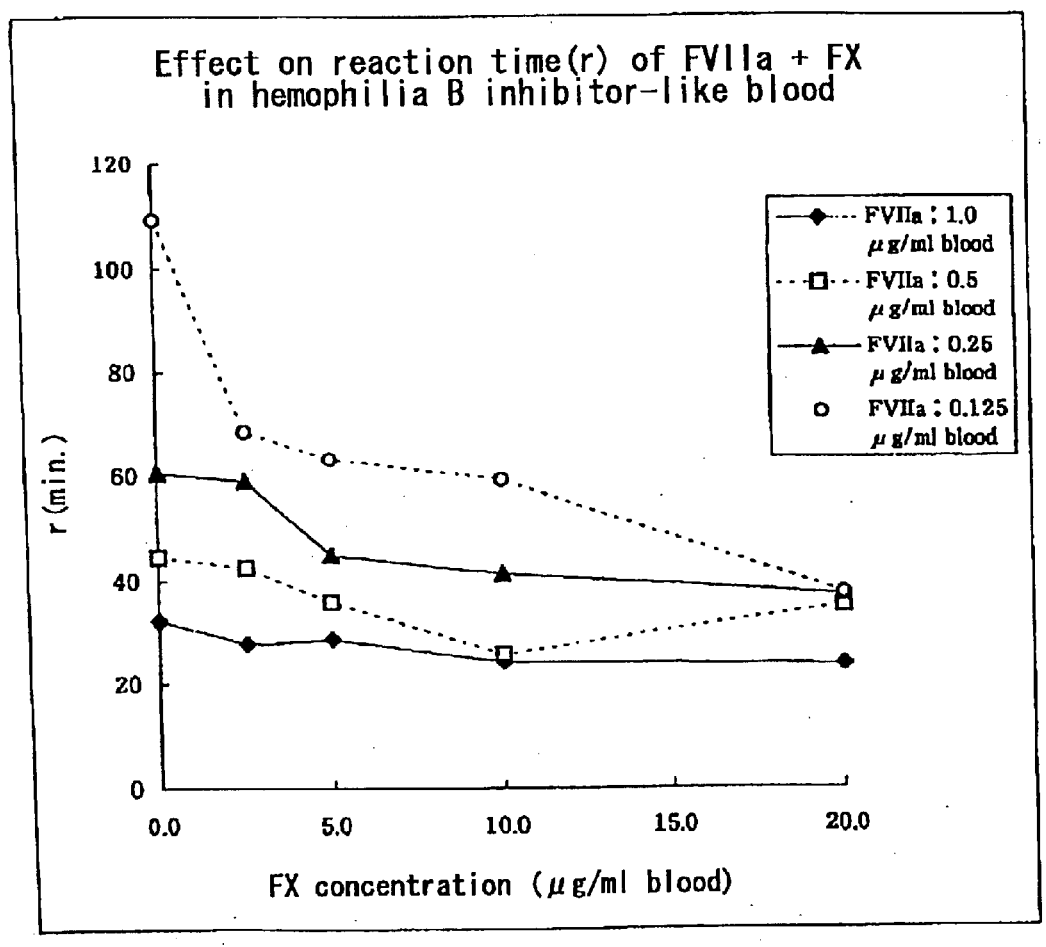
FIG. 7 is a graph showing effects of FVIIa+FX on TEG parameter "r" (reaction time) in hemophilia B inhibitor-like blood.
Figure 8:
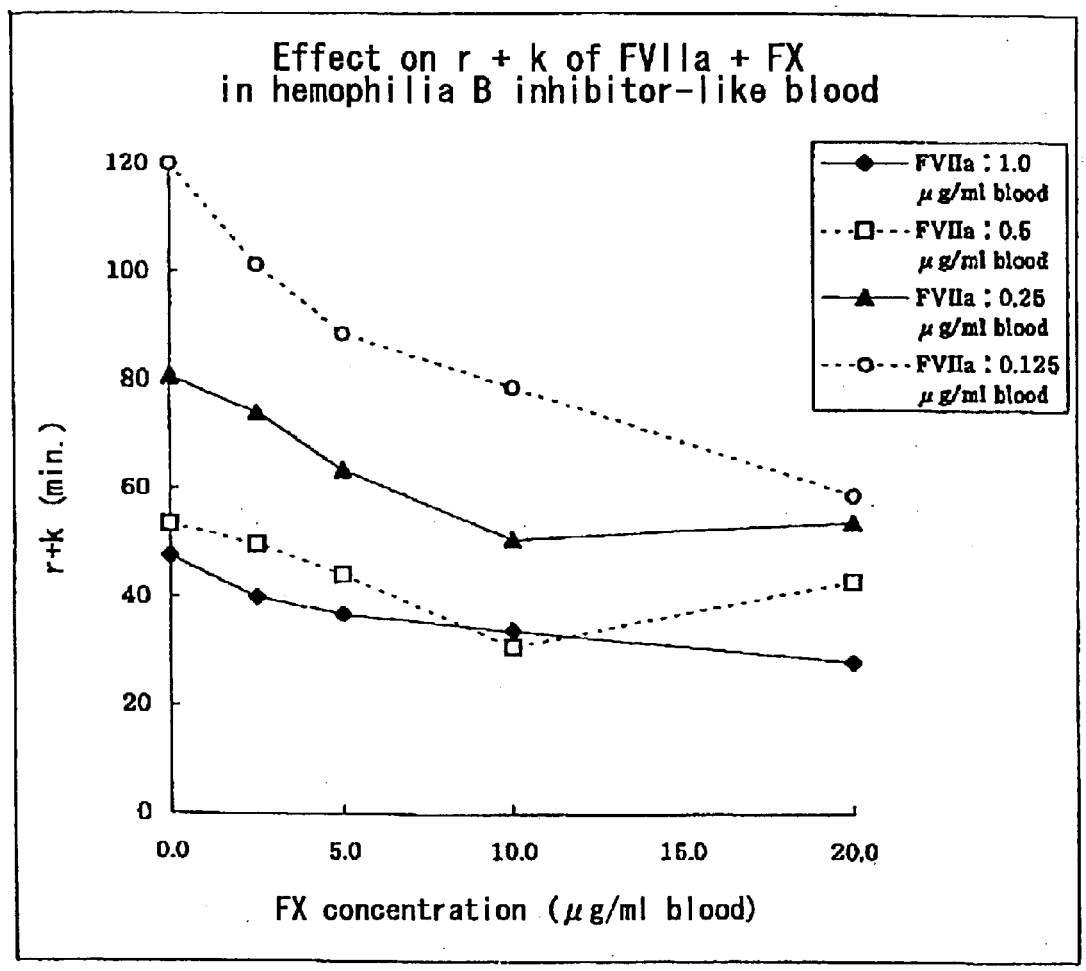
FIG. 8 is a graph showing effects of FVIIa+FX on TEG parameter "r+k" (reaction time+coagulation time) in hemophilia B inhibitor-like blood.
Figure 9:
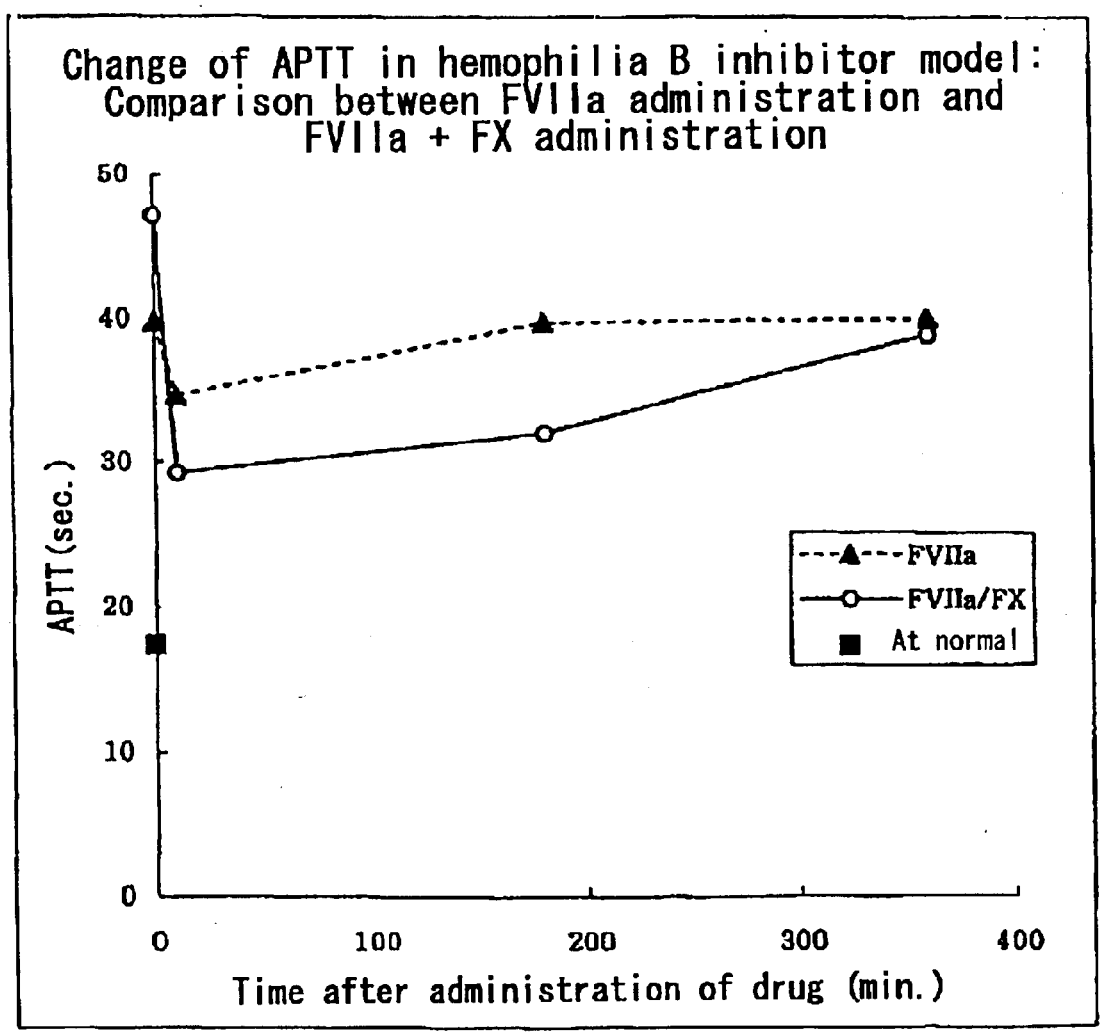
FIG. 9 is a graph showing comparison between administration of FVIIa alone and administration of FVIIa+FX for APTT in hemophilia B inhibitor animal model.
Figure 10:
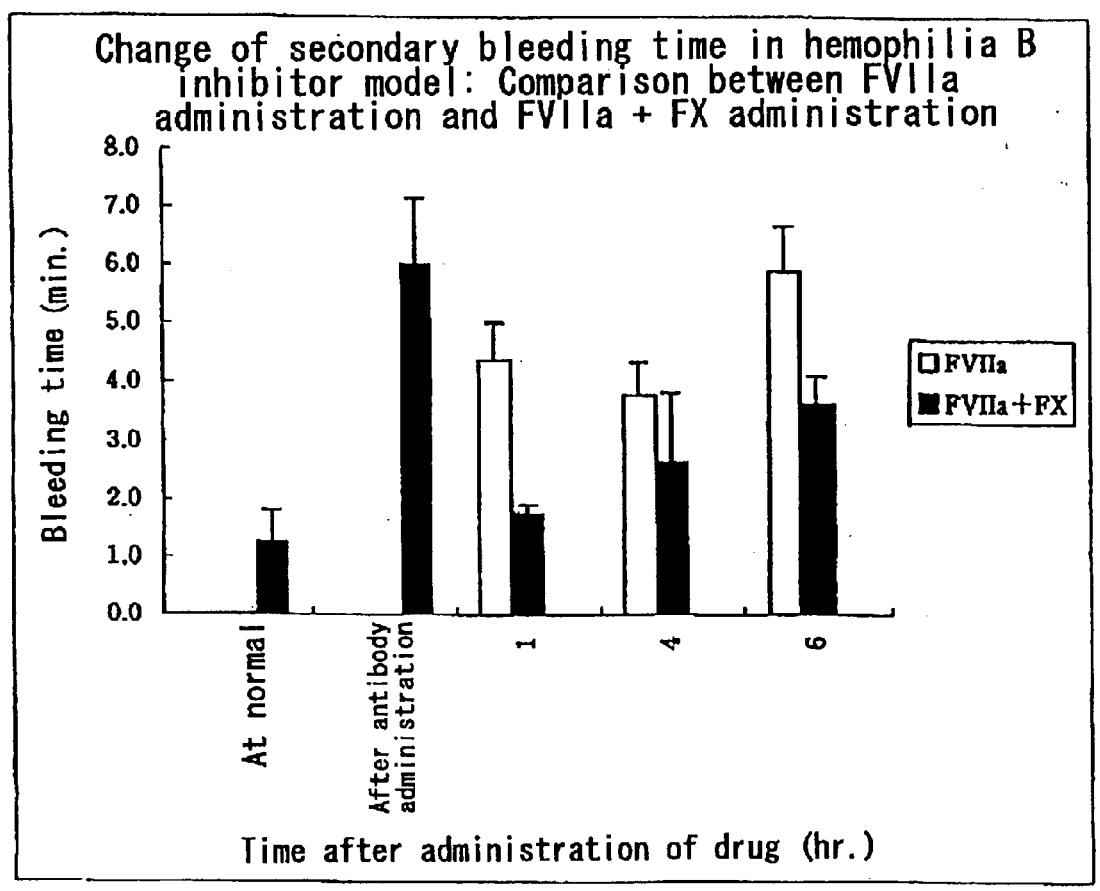
FIG. 10 is a graph showing comparison between administration of FVIIa alone and administration of FVIIa+FX for secondary bleeding time in hemophilia B inhibitor animal model.
Figure 11:
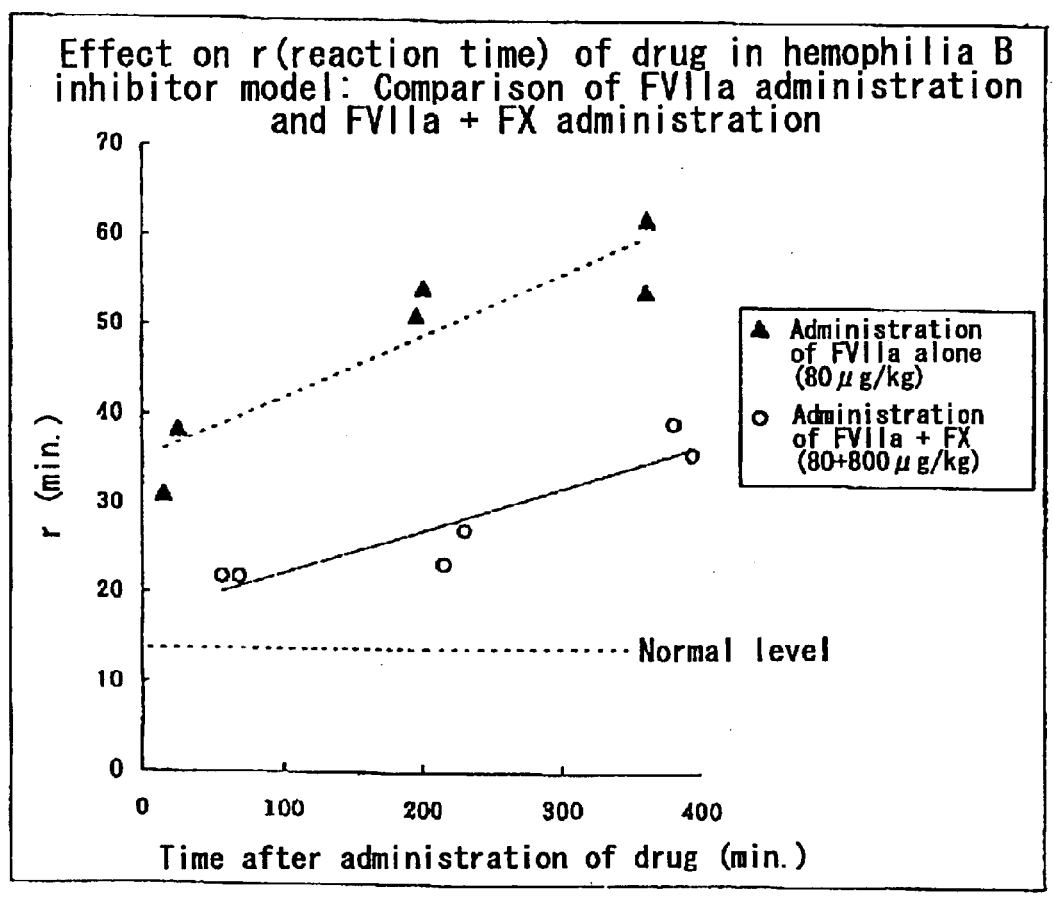
FIG. 11 is a graph showing comparison between administration of FVIIa alone and administration of FVIIa+FX for TEG parameter "r" (reaction time) in hemophilia B inhibitor animal model.
Figure 12:
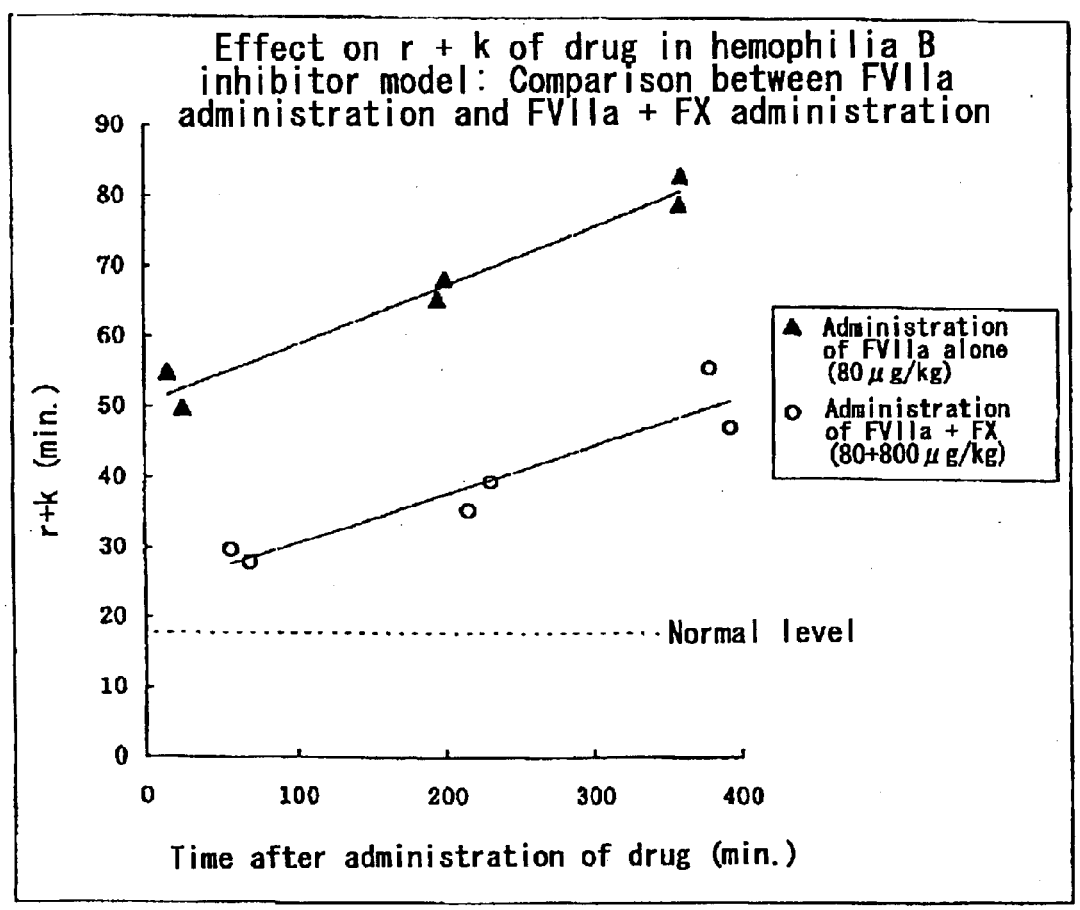
FIG. 12 is a graph showing comparison between administration of FVIIa alone and administration of FVIIa+FX for TEG parameter "r+k" (reaction time+coagulation time) in hemophilia B inhibitor animal model.

Based on the principle as mentioned above, antihuman FIX goat antibody was added to human blood to prepare hemophilia B inhibitor-like blood wherein "r" and "r+k" were prolonged for more than 120 minutes and to an immeasurable degree, respectively. To this hemophilia B inhibitor-like blood were added FVIIa and FX at a concentration of 0.125 to 1 µg/ml blood and 2.5 to 20 µg/ml blood, respectively. As a result, it was shown that "r" and "r+k" were shortened in a manner dependent to a concentration of FVIIa and FX, demonstrating that coagulating capacity of blood, which has been lost in hemophilia B inhibitor-like blood, was corrected by FVIIa and FX. The results are shown in FIGS. 7 and 8.

EXAMPLE 3
Estimate of for Hemostatic Potency the Composition of the Present Invention by Animal Model:

This example was performed with hemophilia B inhibitor model prepared by administering anti-human FIX goat antibody to cynomolgus monkey. The hemophilia B inhibitor model exhibits prolongation of APTT and bleeding time, extreme prolongation of TEG parameters "r" (reaction time) and "r+k" (k: coagulation time), and reduction of maximum amplitude (ma).

Hemophilia B inhibitor model was prepared by administering anti-human FIX goat antibody by rapid intravenous injection and intravenous drip injection to cynomolgus monkey. Effects of administration of FVIIa alone (80 µg/kg) and a combination of FVIIa and FX (each 80 µg/kg and 800 µg/kg) were compared for (1) APTT, (2) bleeding time and (3) TEG. The results are shown in FIGS. 9, 10, and 11 to 12.

It was found that APTT was shortened after administration of the drug (FVIIa alone or in combination with FX) wherein APTT was much more shortened by a combination of FVIIa and FX than FVIIa alone.

Bleeding time was measured as follows: Cynomolgus monkey was cut at tail, about 15 cm apart from the base of tail, to the direction parallel to tail, with Simplate II R (manufactured by Organon Teknika) while evading the artery and vein. Blood pressure cuff was wound round the base of tail and cut was made twice under the pressure of 40 mmHg and bleeding time was measured (primary bleeding time). Oozing blood was blotted off with filter paper without touching the wound. For measuring secondary bleeding time, once bleeding was stopped, the wound was rubbed thrice with cotton sheet to bleed and bleeding time was measured as described for primary bleeding time.

It is known that primary bleeding time usually reflects hemostatic reaction by platelets. Indeed, primary bleeding time was only slightly, but not remarkably, prolonged as compared to normal conditions after administration of anti-human FIX goat antibody. On the contrary, secondary bleeding time was markedly prolonged after administration of anti-human FIX goat antibody but shortened by FVIIa administration or simultaneous administration of both FVIIa and FX. In comparison of effects, bleeding time was improved to much more approach normal conditions and improvement in bleeding time was maintained for a longer period of time with simultaneous administration of both FVIIa and FX than with administration of FVIIa alone.

Similarly, TEG parameters "r" and "r+k" were improved to much more approach normal conditions and effects were maintained for a longer period of time with simultaneous administration of both FVIIa and FX than with administration of FVIIa alone.

What is claimed is:

1. A pharmaceutical composition for treatment of hemorrhage associated with blood coagulation disorders, comprising:

an active ingredient component consisting of activated Factor VII and Factor X as active ingredients; and a pharmaceutically acceptable excipient component, wherein said blood coagulation disorders are disorders of blood coagulation factors including deficiency of blood coagulation factors, especially, blood coagulation disorders manifesting hemostatic disorders caused by inhibitors (antibodies) against blood coagulation factors.

2. The pharmaceutical composition of claim 1, wherein the composition comprises activated Factor VII at a concentration of 1 $\mu$g/ml or more and Factor X at a concentration of 20 $\mu$g/ml or more as active ingredients.

3. The pharmaceutical composition of claim 1, wherein said composition is administered at a dose of 5 to 160 $\mu$g/body weight (kg) of activated Factor VII and 50 to 1,600 $\mu$g/body weight (kg) of Factor X for effecting hemostasis.

4. A method for treating hemorrhage associated with blood coagulation disorders, comprising:

administering a composition comprising an active ingredient component consisting of a combination of activated Factor VII and Factor X and a pharmaceutically acceptable excipient component to patients suffering from hemorrhage associated with blood coagulation disorders, wherein said blood coagulation disorders are disorders of blood coagulation factors including deficiency of blood coagulation factors, especially, blood coagulation disorders manifesting hemostatic disorders caused by inhibitors (antibodies) against blood coagulation factors.

5. The method of claim 4 wherein 5 to 160 $\mu$g/body weight (kg) of activated Factor VII and 50 to 1,600 $\mu$g/body weight (kg) of Factor X are administered.

* * * * *